United States Patent [19]

Hsiao

[11] Patent Number: 4,587,118

[45] Date of Patent: May 6, 1986

[54] DRY SUSTAINED RELEASE THEOPHYLLINE ORAL FORMULATION

[75] Inventor: Chiin H. Hsiao, Cooper City, Fla.

[73] Assignee: Key Pharmaceuticals, Inc., Miami, Fla.

[21] Appl. No.: 680,703

[22] Filed: Dec. 12, 1984

Related U.S. Application Data

[63] Continuation-in-part of Ser. No. 592,935, Mar. 23, 1984, which is a continuation-in-part of Ser. No. 372,300, Apr. 27, 1982, abandoned, which is a continuation of Ser. No. 283,446, Jul. 17, 1981, abandoned.

[51] Int. Cl.$^4$ .................... A61K 9/52; A61K 9/58; A61K 9/62
[52] U.S. Cl. ........................ 424/19; 424/21; 424/35; 514/263; 514/962; 514/964
[58] Field of Search ................ 424/19–22, 424/32–38, 253; 514/962, 964, 263

[56] References Cited

U.S. PATENT DOCUMENTS

| | | | |
|---|---|---|---|
| 2,811,483 | 10/1957 | Aterno et al. | 167/81 |
| 2,853,420 | 9/1958 | Lowey | 167/82 |
| 2,928,770 | 3/1960 | Bardani | 167/82 |
| 3,080,294 | 3/1963 | Shepard | 424/21 |
| 3,081,233 | 3/1963 | Enz et al. | 167/82 |
| 3,109,775 | 11/1963 | Shepard et al. | 167/82 |
| 3,247,066 | 4/1966 | Milosovich | 167/82 |
| 3,344,029 | 9/1967 | Berger | 167/82 |
| 3,400,185 | 9/1968 | Kohnle et al. | 264/117 |
| 3,835,221 | 9/1974 | Fulberth et al. | 424/20 |
| 3,922,339 | 11/1975 | Shear | 424/34 |
| 4,016,254 | 4/1977 | Seager | 424/80 |
| 4,083,943 | 4/1978 | Benedickt | 424/19 |
| 4,085,214 | 4/1978 | Higuchi et al. | 424/253 |
| 4,173,626 | 11/1979 | Dempski et al. | 424/19 |
| 4,248,858 | 2/1981 | Guley et al. | 424/19 |

FOREIGN PATENT DOCUMENTS 109438  1/1940  Australia ............................ 424/20

OTHER PUBLICATIONS

Weinberger, J. Pediatrics 92(1):1–7 Jan. 1978, Theophylline for Treatment of Asthma.
Green et al., J. Pediatrics 98(5):832–834 May 1981 Absorption Characteristics of Sustained Release Theophylline Capsules Administered in Applesauce.
1983 USP-D1-Advice for the Patient, vol. II, pp. 759–760, Jul. 1982 "Xanthines".
1983 USP-D1-Drug Information for the Health Care Provider, vol, I, pp. 921–929, Jul. 1982 "Xanthines".

*Primary Examiner*—Shep K. Rose
*Attorney, Agent, or Firm*—Sybil Meloy; Ronald G. Ort

[57] ABSTRACT

A dry sustained release oral dosage formulation of theophylline and a method of orally administering theophylline is disclosed. The oral formulation is comprised of a capsule which includes upper and lower parts which are connectible and easily separable from each other, and a plurality of micropellets present in the capsule. The micropellets provide sustained release of theophylline when taken by a patient and are comprised of inner seeds coated with a mixture of theophylline and polyvinylpyrrolidone which is further coated with a mixture of ethylcellulose and hydroxypropylcellulose. The oral dosage formulation is administered by separating the upper and lower parts of the capsule and placing the micropellets on a food which is preferably soft to the extent of not requiring chewing and then eating the food with the micropellets thereon. The micropellets have sufficient size so that they can be seen, but are sufficiently small so that they are not easily detected in the mouth in combination with the food and can be swallowed without difficulty.

7 Claims, No Drawings

DRY SUSTAINED RELEASE THEOPHYLLINE ORAL FORMULATION

CROSS-REFERENCES

This application is a continuation-in-part of application Ser. No. 592,935, filed Mar. 23, 1984, which, in turn, is a continuation-in-part of application Ser. No. 372,300, filed Apr. 27, 1982 and now abandoned, which in turn, is a continuation of application Ser. No. 283,446, filed July 17, 1981 and now abandoned.

BACKGROUND OF THE INVENTION

A zero order release theophylline product, THEO-DUR, has received widespread acceptance in the marketplace and among the medical profession as a bronchodilator. However, THEO-DUR is in the form of a dry tablet formulation which cannot be easily swallowed by certain individuals. Specifically, children and elderly patients often have difficulty swallowing tablets. Accordingly, there is a need to provide a sustained release bronchodilator which is in a dry form, but which can be more easily administered to individuals having difficulty in swallowing, such as children and elderly patients. In addition, there is a need for a method for orally administering any such dry formulation in a manner which will be acceptable to children and elderly patients.

U.S. Pat. No. 3,344,029 to Berger et al discloses a sustained release composition which can include a theophylline salt as an active ingredient. Finely divided active ingredients such as theophylline salt can be mixed with a powdered sugar and corn starch. This mixture can be combined with other ingredients such as polyethylene glycol to form material which is forced through a mesh screen to form cores (see column 3, lines 5-30). The cores are then placed into a coating pan and are coated and dried (see column 3, line 55-column 5, line 30).

U.S. Pat. No. 3,109,775 discloses a theophylline-noscapine sustained released composition which is used in the treatment of asthma or other bronchial disorders. The composition can be comprised of an inner core which is coated with an inactive ingredient such as sucrose or cellulose combined with the active ingredients (see column 8, lines 36-54). A fat-wax can be utilized as a retardant to obtain sustained release of the active ingredients (see column 7, line 39).

U.S. Pat. No. 4,321,253 discloses a suspension of microencapsulated bacampicillin acid addition salt for oral, especially pediatric administration. The patent discloses the formation of micropellets which are placed into an aqueous suspension and then administered to a patient. Since the microcapsules are placed in an aqueous solution, the active ingredient can start being released to solution immediately and the amount of active ingredient released to the solution could increase with time. This could render the solution bitter and children may be reluctant to take such a "medicine". Furthermore, the accurate dosing of a suspension is more difficult to obtain, since the suspension is usually measured by a tea or tablespoon and a tea or tablespoon full made very widely in size. The inability to know the exact dose of the pharmaceutically active drug in combination with the inability to determine how much was released to the solution is a particularly big problem with respect to the drug theophylline which has a very narrow therapeutic window.

U.S. Pat. No. 3,835,221 discloses an orally administrable drug dosage form which has delayed action. The dosage form is comprised of small globules which are provided with a release-delaying coating. The active substance is applied to small inert essentially round globules which are coated in such a manner so as to provide delayed release of the active ingredient. The coating may include materials such as polyvinyl acetate which may be combined with another material such as ethyl cellulose.

U.S. Pat. No. 4,083,949 discloses a new oral form of medication and a method for producing it. The oral form disclosed releases the active ingredient in the gastrointestinal tract at a constant rate. The dosage form may be comprised of spheroidal shaped particles of active ingredient which are coated with materials such as ethyl cellulose in order to provide sustained release of the active ingredient.

Although each of the dosage forms described in the patents referred to above may offer advantages with respect to delivery the active ingredient to the patient, each of the disclosures does not take into consideration all of the factors which must be considered when attempting to provide the correct therapeutic blood level of theophylline to a young or elderly patient via an oral formulation. Accordingly, each of the above referred to formulations suffers from one or more disadvantages thus indicating a clear need for an oral dosage formulation such as that being presented herein by the present inventor.

As indicated above, THEO-DUR has received widespread acceptance in the marketplace and among medical professions. One of the main reasons for its widespread acceptance is that the THEO-DUR product provides a constant therapeutic blood level of theophylline. Accordingly, the desired bronchodilator effect is obtained, but the undesirable side effects from too much theophylline are avoided. The concept of the present invention is to provide the same zero order release concept with a product which can be more easily administered to patients who are reluctant to take tablets.

SUMMARY OF THE INVENTION

An object of the present invention is to provide a dry sustained release theophylline oral formulation in the form of micropellets enclosed within a dry capsule.

Another object of the present invention is to provide a dry sustained release theophylline oral formulation comprised of micropellets which when ingested will provide zero order release of theophylline in the human body.

Yet another object of the invention is to provide a method for administering a dry zero order sustained release theophylline product to a patient whereby micropellets capable of zero order release of theophylline are placed on an edible food substance and then consumed by the patient.

The dry oral sustained release theophylline formulation of the present invention is comprised of micropellets provided within an easy to open capsule. The micropellets are provided by coating sugar seeds with a mixture of theophylline and polyvinylpyrrolidone. The theophylline coated sugar seeds are then coated with a mixture of ethyl cellulose and hydroxypropylcellulose. The hydroxypropyl cellulose is water soluble and its presence on the micropellets as a coating provides "channels" which allow for the release of the theophylline when the micropellets come in contact with an aqueous environment such as in the gastrointestinal tract.

DETAILED DESCRIPTION OF THE INVENTION

The dry sustained release theophylline oral formulation of the present invention is comprised of a plurality of micropellets which are contained within a capsule. The capsule can be easily opened and the micropellets placed on a food substance for oral administration. Alternatively, the capsules can be swallowed. Any number of micropellets can be present within the capsule provided their numbers in relation to their size and surface area results in providing therapeutic blood levels of theophylline. It is desirable that the micropellets are sufficiently small such that their presence within the mouth is not easily discernible, but sufficiently large so that they can be seen when placed on food. Accordingly, there are typically less then 1000 micropellets within each capsule, preferably 800–900 micropellets in each pellet, and particularly preferably about 845 micropellets within a capsule provided the capsule is containing a 100 milligram dose of theophylline.

The micropellets of the invention are provided by coating theophylline in micronized form onto a sugar seed having a 60/80 mesh. The theophylline is coated onto the sugar seed by first combining it with polyvinylpyrrolidone, having a molecular weight of from about 30,000 to about 50,000 with a molecular weight of about 40,000 being preferred. The sugar seeds which are coated with a combination of theophylline and polyvinylpyrrolidone are then in turn coated with an outer coating comprised of two polymers. More specifically, the sugar seeds coated with theophylline are then coated with from 5% to 10% by weight of sustained release coating which is comprised of a combination of ethylcellulose and hydroxypropylcellulose. More specifically, the sustained release coating is comprised of 70% to 90% by weight of ethylcellulose and 10% to 30% hydroxypropylcellulose based on the weight of the coating. In a preferred embodiment of the present invention, the outer coating is comprised of 75% ethylcellulose and 25% hydroxypropylcellulose. Furthermore, in a preferred embodiment of the invention, the average diameter of each of the micropellets formed is 0.5 to 0.7 mm, particularly preferably about 0.6 mm. This size is particularly desirable in that the patient cannot normally differentiate pellets of this size from other food matter contained in the mouth. However, they are sufficiently large such that if they are sprinkled onto food, their presence can be seen with the naked eye. Accordingly, one could determine if all of the theophylline sprinkled onto food was eaten by the patient.

When prescribing theophylline it is important that:

(1) the patient be able to take the theophylline product, i.e. the oral formulation can be swallowed;

(2) a determination can be made that all of the theophylline formulation prescribed has been taken, i.e. that a portion has not remained unswallowed; and (3) that after swallowing the oral formulation, the theophylline is released slowly so as to provide zero order release of theophylline and a constant blood level of theophylline sufficiently high to cause bronchodilation, but sufficiently low to avoid any serious side effects.

In order to provide a formulation which children and elderly patients can easily take, the present inventor has determined that the best way to provide the formulation is in the form of micropellets, having a size in the range of 0.5 to 0.7 mm and particularly preferably 0.6 mm. In order to make it possible to determine that all of the prescribed theophylline has been taken by the patient, the present inventor has determined that it would be best to place these micropellets onto a food substance which has a color that is distinguishable from the color of the pellets. Due to the size of the pellets and the difference in color between them, and the food which they are placed on, a determination can be made as to whether all of the theophylline has been taken by the patient. Accordingly, factors such as the size of the pellets, the difference in color between the pellets and the food they are placed on, and the ease of opening of the capsules containing the pellets, all contribute to assuring that the patient can take the theophylline oral formulation and that all of the formulation is taken.

Once the oral formulation has been taken and it is confirmed that all of the prescribed dosage has been swallowed by the patient, the problem remains with respect to providing an oral formulation which is capable of sustained release of the theophylline in such a manner that a constant blood level of theophylline is maintained. In order to achieve the desired "zero order release" of theophylline with the present formulation, the present inventor formulated the micropellets of the present invention. These micropellets are comprised of 5% to 10% by weight of a coating of two different polymers. One of the polymers is ethylcellulose with is present in the coating in an amount of 90% to 70% by weight, based on the weight of the coating. The other polymer is hydroxypropylcellulose which is present in an amount of 10% to 30% by weight, based on the weight of the coating. When a coating is comprised in this manner and placed on a micropellet as described in detail below, the oral formulation of the invention will provide zero order release of theophylline.

It is important to note that all of the factors with respect to administering theophylline are interrelated. More specifically, it is important to note that the dry oral formulation provided must be one which the patient can take and for which it can be determined that all of it was taken, and after administration provide zero order release of the theophylline. If the size of the pellets is made too small, they cannot be seen and if they are made too large, they are detectable in the mouth and may not be swallowed by the patient. If the micropellets are made too small or they are placed on food having the same color, or placed in a liquid, it is not possible to determine whether the patient has ingested all of the prescribed drug. If the micropellets do not provide zero order release, then the blood level of theophylline may be too low or too high at particular times after administration. Accordingly, factors such as the size of the micropellets, the amount and composition of the coating of the micropellets and the discernibility of the micropellets on food are all interrelated to each other to provide the oral formulation of the present invention.

If the micropellets of the present invention were coated with a coating comprised completely of ethylcellulose (which is an ethyl ether of cellulose) containing 2.25–2.28 ethoxyl groups per anhydroglucose unit, the drug within the coating would be released very slowly or be released not at all for a long period of time. Accordingly, micropellets having such an ethylcellulose coating would not provide the desired availability of the theophylline contained in such micropellets.

The inclusion of hydroxypropylcellulose within the coating along with the ethylcellulose provides the desired sustained release of the active ingredient theophylline. Hydroxypropylcellulose, wherein the primary hydroxyls present in cellulose have been substituted (etherified) by hydroxypropyl is more water soluble then ethylcellulose. Accordingly, the presence of such hydroxypropylcellulose in the coating provides "channels" in the coating through which water can enter, and over a period of time, leach out the theophylline contained within the non-pareil sugar seed. The presence of too many "channels" will make the theophylline more quickly available then is therapeutically appropriate. Within the stated range, an optimal release rate is obtained when the outer coating contains three parts of ethylcellulose (75% by weight) to one part of hydroxypropyl cellulose (25% by weight).

The following non-limiting examples further illustrate the invention:

EXAMPLE 1

3.2 Kilograms polyvinylpyrrolidone, molecular weight 40,000 (Kollidon 30) is dissolved in 32 liters of isopropanol and 12.8 kilograms of micronized theophylline is dispersed therein. 4.0 kilograms of sugar, 60/80 mesh is placed in the Wurster air suspension coating column. After the air suspension system is in operation with the sugar, the dispersed theophylline is sprayed into the column with the inlet air having a temperature of 60° C., the spray pressure at 4 bars, and the spray rate being 100 ml/min. After completion of the above procedure, operation of the Wurster column is stopped, and the product reserved as "theophylline pellets, Active I".

A second 3.2 kilogram batch of polyvinylpyrrolidone, molecular weight 40,000 (Kollidon 30) is dissolved in 32.0 liters of isopropanol, and dispersed into the resultant mixture is 12.8 kilograms of micronized theophylline. 4.0 kilograms of "theophylline pellets, Active I" are then charged into the same Wurster column under the same conditions of temperature and pressure, and at the same rate. The second batch having the theophylline dispersed therein is then charged into the Wurster column to further build up the coating. The Wurster column is emptied and the product labelled "Theophylline pellets, Active II".

A coating mixture of 13.2 liters of chloroform and 3.3 liters of methanol is prepared, into which are dispersed 992.0 grams of ethylcellulose (Ethocel N-10 Dow) and 329.0 grams of hydroxypropyl cellulose (Hercules, Klucel LF). Into the Wurster column is charged 19.0 kilograms of "Theophylline pellets, Active II", which are then coated with the coating mixture under conditions of 30° C., spray pressure 3 bars and spray rate 100 ml/min. The resultant coated pellets are small white micropellets which may be placed into capsules containing the desired dosage unit.

EXAMPLE 2

Using a procedure similar to that described in Example 1, theophylline pellets were outer coated with 5% by weight of a mixture containing 75% by weight ethylcellulose and 25% by weight hydroxypropylcellulose.

The release characteristics of the coated pellets were measured according to the U.S.P. XX dissolution procedure (one hour in simulated gastric fluid followed by simulated intestinal fluid). The results obtained are tabulated below:

| Time (hrs) | Cumulated % Release |
|---|---|
| 1 | 12 |
| 2 | 25 |
| 4 | 57 |
| 6 | 81 |
| 8 | 96 |

The release characteristics observed over an eight hour period are relatively consistent and uniform in terms of amount of theophylline released per unit time.

COMPARATIVE EXAMPLE

Using a procedure similar to that described in Example 1, theophylline pellets were outer coated with 5% by weight of ethylcellulose. When the release characteristics of the coated pellets were measured according to the U.S.P. XX dissolution procedure, considerably less than 20% of the theophylline was released after eight hours.

The presence of at least 10% by weight hydroxypropylcellulose in the outer coating is required to impart the desirable sustained release characteristics to the micropellets of the invention. However, the presence of more than 30% by weight of hydroxypropylcellulose would have the therapeutically undesirable and potentially dangerous result of making the theophylline available too quickly unless an impractically excessive amount of coating is applied.

The pellets of the present invention may be provided in a container such as a capsule, or compressed optionally with the addition of tableting aids such as microcrystalline cellulose and magnesium stearate. The capsule embodiment of the present invention is particularly advantageous for pediatric and geriatric patients who may be either unable or unwilling to swallow a large sustained release tablet. For pediatric administration, it is particularly contemplated that the individually coated polymeric pellets are administered in food, which is then taken as part of a meal, to provide the sustained theophylline effect.

While the invention has been described in detail with reference to specific embodiments thereof, it will be apparent to one skilled in the art, that various changes and modifications can be made therein without departing from the spirit and scope thereof.

What is claimed is:

1. A sustained release dosage formulation of theophylline which includes an easily openable capsule having therein a plurality of micropellets, the sum of such micropellets in said capsule forming a dosage unit of theophylline, each of said micropellets being based upon a seed having coated thereon a first coating mixture of theophylline and polyvinylpyrrolidone, characterized in that the thus coated seed has further coated thereon a second coating mixture of about 90–70% by weight of ethylcellulose and about 10–30% by weight of hydroxypropylcellulose.

2. The dosage formulation of claim 1 further characterized in that the weight of the second coating mixture is about 5–10% of the weight of the micropellets before such coating is applied.

3. The dosage formulation of claim 1 further characterized in that the second coating mixture contains about 3 parts of ethylcellulose to 1 part of hydroxypropylcellulose.

4. The dosage formulation of claim 1 further characterized in that said polyvinylpyrrolidone has a molecular weight of about 30,000 to about 50,000.

5. The dosage formulation of claim 4 further characterized in that said polyvinylpyrrolidone has a molecular weight of about 40,000.

6. The dosage formulation of claim 1 further charcterized in that said seed is sugar having a mesh size of 60/80.

7. The dosage formulation of claim 1 further characterized in that said micropellets have diameters in the range of about 0.5 to about 0.7 mm.

* * * * *